United States Patent [19]

Chaudhari et al.

[11] Patent Number: 6,028,227

[45] Date of Patent: Feb. 22, 2000

[54] SINGLE STEP PROCESS FOR THE PREPARATION OF P-AMINOPHENOL

[75] Inventors: Raghunath Vitthal Chaudhari; Sunil Sadashiv Divekar; Manisha Jagdeeshrao Vaidya; Chandrashekar Vasant Rode, all of Maharashtra, India

[73] Assignee: Council of Scientific & Industrial Research, New Delhi, India

[21] Appl. No.: 09/257,107

[22] Filed: Feb. 24, 1999

[30] Foreign Application Priority Data

Feb. 12, 1999 [IN] India .............................. 243/DEL/99

[51] Int. Cl.[7] .................................................. C07L 209/00
[52] U.S. Cl. .............................................................. 564/418
[58] Field of Search .............................................. 564/418

[56] References Cited

U.S. PATENT DOCUMENTS

| | | |
|---|---|---|
| 3,328,465 | 6/1967 | Spiegler . |
| 3,383,416 | 5/1968 | Benner . |
| 3,953,509 | 4/1976 | Greco . |
| 4,307,249 | 12/1981 | Derrenbacker . |
| 4,885,389 | 12/1989 | Lee et al. . |
| 5,545,754 | 8/1996 | Klausener et al. . |

FOREIGN PATENT DOCUMENTS

| | | |
|---|---|---|
| 854732 | 10/1970 | Canada . |
| 1056158 | 3/1986 | Japan . |
| 713622 | 8/1954 | United Kingdom . |
| 856366 | 12/1960 | United Kingdom . |
| 1028078 | 5/1966 | United Kingdom . |
| 1181969 | 2/1970 | United Kingdom . |

*Primary Examiner*—Paul J. Killos
*Attorney, Agent, or Firm*—Ladas & Parry

[57] ABSTRACT

The present invention provides a single step process for the preparation of p-aminophenol by contacting a mixture of nitrobenzene and water with hydrogen over a solid acid catalyst, terminating the reaction to obtain a reaction mixture containing the product, extracting the reaction mixture with an organic solvent, separating the aqueous layer containing the product, and then concentrating the aqueous layer by any conventional method to obtain the product.

6 Claims, No Drawings

SINGLE STEP PROCESS FOR THE PREPARATION OF P-AMINOPHENOL

FIELD OF THE INVENTION

The present invention relates to an improved single step process for the preparation of p-aminophenol. More particularly, the process relates to the preparation of p-aminophenol in an aqueous medium using solid acid catalyst instead of mineral acid medium.

BACKGROUND OF THE INVENTION p-Aminophenol (PAP) is a well-known and very useful industrial chemical. It is used as an intermediate in the production of pharmaceuticals such as paracetamol, in the production of dyestuffs such as sulfur dyes and in making photographic chemicals.

Conventionally, PAP is prepared by hydrolysing p-nitrochlorobenzene to p-nitrophenol. Then hydrogenation of nitrophenol to PAP is carried out using Fe/HCl catalyst. In this multi-step process, quantity of iron (catalyst precursor) required is quite large, subsequently the production of iron sludge is very large, posing a serious effluent problem. The work up of reaction crude is cumbersome. The quantity of iron used is very important for the faster reduction rate.

An important commercial process for the preparation of p-aminophenol involves the catalytic hydrogenation of nitrobenzene in a strongly acidic medium utilising supported platinum based catalysts. In this process, phenylhydroxylamine (PHA) is first formed and this intermediate immediately rearranges in the presence of acid medium to PAP. Other by-products formed are aniline and o-aminophenol.

The second step involves the rearrangement of phenylhydroxylamine to PAP in an acidic medium. In conventional processes, concentrated sulphuric acid is used. In actual practice, both these steps are carried out in a single reactor. The reaction mixture consists of both aqueous as well as organic phases.

In prior art, Brenner (U.S. Pat. No. 3,383,416, 1969) observed that the interruption of the hydrogenation step before all nitrobenzene is consumed helps in the suspension of the catalyst in the nitrobenzene layer. This is advantageous since the aqueous reaction mixture is immiscible with the nitrobenzene layer and the aqueous layer containing PAP, aniline and other minor by-products is readily separated from the catalyst-nitrobenzene layer by decantation. The PAP is then recovered from the aqueous layer and further purified.

Hydrogenation of nitrobenzene to PAP in acetic acid containing $CF_3SO_3H$ using Pt/C catalyst is reported (EP 5,58,369, 1992). Lower yield and selectivity are obtained when $H_3PO_4$ is used instead of $CF_3SO_3H$ in acetic acid medium.

Greco (U.S. Pat. No. 3,953,509, 1976) reported the use of molybdenum sulphide on carbon catalyst for the hydrogenation of nitrobenzene to PAP. Dunn (U.S. Pat. No. 4,264,529, 1981) has reported the use of platinum on (—alumina for the hydrogenation of nitrobenzene to yield PAP. Gaskey and Chapman (U.S. Pat. No. 4,415,753, 1983) and (U.S. Pat. No. 4,571,437, 1986) have suggested low temperature hydrogenation in the presence of a modified catalyst system containing a sulphur compound and the rearrangement step in a separate vessel. Recently, a process has been described by Landsheidt et al. (U.S. Pat. No. 5,302,742, 1994) in which hydrogenation of substituted nitrobenzene (p-position vacant) is carried out in the presence of a co-solvent (in acidic medium with 5% Pt/C and an acylating agent to give corresponding N-acylated p-amino phenols.

Rylander et al. (U.S. Pat. No. 3,715,397, 1973) disclosed a process for the preparation of PAP by catalytic hydrogenation of nitrobenzene in a sulphuric acid medium in the presence of dimethyl sulphoxide, using platinum oxide catalyst.

Generally, nitrobenzene, when first reduced to form PHA, can be further reduced to form aniline. In the presence of acid, PHA undergoes rearrangement to form PAP. As noted, after the formation of PHA, there are two pathways leading to the final products PAP and aniline.

In accordance with this invention, it has now been discovered that the solid acid can be used as an alternative for mineral acid, in the rearrangement of PHA to PAP. The hydrogenation of nitrobenzene is complete and PAP is formed along with aniline.

OBJECT OF THE INVENTION

The object of the present invention is to provide a single step process for the preparation of p-aminophenol using solid acid catalyst.

SUMMARY OF THE INVENTION

The present invention provides a single step process for the preparation of p-aminophenol by contacting a mixture of nitrobenzene and water with hydrogen over a solid acid catalyst, terminating the reaction to obtain a reaction mixture containing the product, extracting the reaction mixture with an organic solvent, separating the aqueous layer containing the product, and then concentrating the aqueous layer by any conventional method to obtain the product.

DETAILED DESCRIPTION OF THE INVENTION

Accordingly, the present invention provides a single step process for the preparation of p-aminophenol which comprises contacting a mixture of nitrobenzene and water with hydrogen over a solid acid catalyst at a pressure ranging between 300 to 400 psi, at a temperature in the range of 50–100° C. for a period of 3 to 7 hours, terminating the reaction to obtain a reaction mixture containing the product, extracting the reaction mixture with an organic solvent, separating the aqueous layer containing the product, concentrating the aqueous layer with conventional methods to obtain the product.

In one of the embodiments of the present invention, the ratio of nitrobenzene to water ranges between 1:5 to 1:7.

In another embodiment, the solid catalyst used are selected from the group consisting of various ion exchange resins, heteropolyacids, synthetic and natural acidic clays and acidic zeolites, preferably from ion exchange resins.

In yet another embodiment, the proportion of the solid acid to the total charge is in the range of 3 to 7%.

In another embodiment, the organic solvent used for the extraction of the reaction mixture may be selected from toluene, cyclohexane, and ethyl acetate.

The present invention describes an alternative process wherein solid acids are used, instead of mineral acids for the rearrangement of PHA to PAP. The use of solid acid such as ion exchange resins H+form, acidic clays, zeolites and heteropolyacids overcome the problems associated with the use of mineral acids.

The process of the present invention is described below with reference to examples. These examples are illustrative and should not be construed to limit the scope of the present invention in any manner.

EXAMPLE 1

PAP was prepared by single step catalytic hydrogenation of nitrobenzene in a stirred 0.3 liter SS autoclave having an automatic temperature controller. A reaction charge was prepared by adding 11.5 gm (93.4 mmol) of nitrobenzene, 90 gm of water, 0.018 gm 1% Pt-S/C catalyst and 3.0 gm ion exchange resin (Indion 130). The reactor was sealed, purged initially with nitrogen and then with hydrogen and was then pressurised with hydrogen to 100 psig. When the reaction temperature of 80° C. was attained, the reactor was further pressurised to 400 psig with $H_2$ and the reaction was commenced by starting the agitation. The temperature was controlled during the reaction in the range of 78–80° C. Hydrogen uptake was monitored with pressure gauge and hydrogen absorption terminated after slightly more than 2 moles of hydrogen per mole of nitrobenzene was consumed. At this point, the hydrogen uptake stopped abruptly indicating the end of the reaction.

After completion of the reaction, the reactor was purged with nitrogen, the reaction mixture was removed from the autoclave and the catalyst and the resin were separated from the reaction mixture by filtration. The filtrate was extracted with toluene. The organic and aqueous layers were analysed for reactants and products using GC and HPLC. The conversion of nitrobenzene was found to be 97% and amount of PAP was found to be 13 mmol with the remainder being aniline.

EXAMPLE 2

In a typical experiment, 11.5 gm (93.4 mmol) of nitrobenzene, 90 gm of water, 0.035 gm of 1% Pt-S/C catalyst and 3.0 gm ion exchange resin (Indion 130) were added to the reactor. The reaction was carried out at 80° C. and hydrogen pressure of 400 psig. After completion of reaction the reactor was cooled, catalyst and resin were separated by filtration and washed with toluene. The filtrate was extracted with toluene. The aqueous and organic phases were analysed by GC and HPLC. The conversion of nitrobenzene was found to be 78%. The amount of PAP obtained was 5 mmol and the rest was aniline.

EXAMPLE 3

In a typical experiment, 11.5 gm (93.4 mmol) of nitrobenzene, 90 gm of water, 0.018 gm of 1% Pt-S/C catalyst and 6.0 gm ion exchange resin (Indion 130) were added to the reactor. The reaction was carried out at 80° C. and hydrogen pressure of 400 psig. After completion of reaction, the reactor was cooled, catalyst and resin were separated by filtration and washed with toluene. The filtrate was extracted with toluene. The aqueous and organic phases were analysed by GC and HPLC. The conversion of nitrobenzene was found to be 75%. The amount of PAP was found to be 4 mmnol and the rest was aniline.

EXAMPLE 4

In a typical experiment, 11.5 gm (93.4 mmol) of nitrobenzene, 90 gm of water, 0.018 gm of 1% Pt-S/C catalyst and 3 gm ion exchange resin (Indion 130) were added to the reactor. The reaction was carried out at 80° C. and hydrogen pressure of 400 psig. After completion of reaction, the reactor was cooled, catalyst and resin were separated by filtration and washed with toluene. The filtrate was extracted with toluene. The aqueous and organic phases were analysed by GC and HPLC. The conversion of nitrobenzene was found to be 98%. The amount of PAP was found to be 2 mmol and the rest was aniline.

EXAMPLE 5

In a typical experiment, 11.5 gm (93.4 mmol) of nitrobenzene, 90 gm of water, 0.018 gm of 3% Pt-S/C catalyst and 3.0 gm ion exchange resin were added to the reactor. The reaction was carried out at 80° C. and hydrogen pressure of 400 psig. After completion of reaction, the reactor was cooled, catalyst and resin were separated by filtration and washed with toluene. The filtrate was extracted with toluene. The aqueous and organic phases were analysed by GC and HPLC. The conversion of nitrobenzene was found to be 100%. The amount of PAP was found to be 4 mmol and the rest was aniline.

EXAMPLE 6

In a typical experiment, 11.5 gm (93.4 mmnol) of nitrobenzene, 90 gm of water, 0.018 gm of 1% Pt-S/C catalyst and 0.2 gm of heteropolyacid ($H_3PV_2Mo_{10}O_{40}$) were added to the reactor. The reaction was carried out at 80° C. and hydrogen pressure of 400 psig. After completion of reaction, the reactor was cooled, catalyst and resin were separated by filtration and washed with toluene. The filtrate was extracted with toluene. The aqueous and organic phases were analysed by GC and HPLC. Total conversion of nitrobenzene was observed with the formation of 3 mmol PAP and the rest was aniline.

The present invention offers the following advantages over the known processes:

For a conventional process using strong mineral acid medium, the material of construction of the reactor should be corrosion resistant—such as hastelloy, tantalum, etc. The present invention provides a method for the preparation of PAP by hydrogenating nitrobenzene in acidic medium, generated by the use of solid acid instead of mineral acid.

A separate step of neutralization is not necessary. In the conventional process, an inorganic salt formation due to neutralization of acid leads to serious environmental problems.

We claim:

1. A single step processor the preparation of p-aminophenol which comprises contacting a mixture of nitrobenzene and water with hydrogen over a solid acid at a pressure ranging between 300 to 400 psi, at a temperature in the range of 50–100° for a period of 3 to 7 hours, terminating the reaction to obtain a reaction mixture containing the product, extracting the reaction mixture with an organic solvent, separating the aqueous layer containing the product, and concentrating the aqueous layer to obtain the product.

2. A process as claimed in claim 1, wherein the ratio of nitrobenzene to water ranges between 1:5 to 1:7.

3. A process as claimed in claim 1, wherein the solid acids used are selected from the group consisting of ion exchange resins, heteropolyacids, synthetic and natural acidic clays, and acidic zeolites.

4. A process as claimed in claim 1, wherein the proportion of the solid acid to the total charge is in the range of 3 to 7%.

5. A process as claimed in claim 1, wherein the organic solvent used for the extraction of the reaction mixture is selected from the group consisting of toulene, cyclohexane, and ethyl acetate.

6. A process according to claim 3 wherein the solid acid is an ion exchange resin.

* * * * *